United States Patent [19]

Yamamoto et al.

[11] Patent Number: 4,564,703
[45] Date of Patent: Jan. 14, 1986

[54] PROCESS FOR PREPARING METHACRYLIC ACID

[75] Inventors: Haruhisa Yamamoto; Shinichi Akiyama, both of Takaoka, Japan

[73] Assignee: Nippon Zeon Co., Ltd., Tokyo, Japan

[21] Appl. No.: 30,647

[22] Filed: Apr. 16, 1979

Related U.S. Application Data

[63] Continuation-in-part of Ser. No. 843,691, Oct. 19, 1977, abandoned.

[30] Foreign Application Priority Data

Oct. 26, 1976 [JP] Japan ................... 51-128665

[51] Int. Cl.$^4$ ........................... C07C 51/25
[52] U.S. Cl. .................... 562/534; 562/532; 562/535; 568/471; 568/477; 568/478; 568/479; 568/480
[58] Field of Search .......... 562/534, 532, 535; 260/603 C, 604 R; 568/471, 477, 478, 479, 480

[56] References Cited

U.S. PATENT DOCUMENTS 3,686,294 8/1972 Ito et al. ................... 562/535
3,976,688 8/1976 Akiyama et al. ............ 562/532
4,031,135 6/1977 Engelbach et al. ......... 562/535
4,035,418 7/1977 Okada et al. ............. 260/603 C
4,129,600 12/1978 Childress et al. .......... 260/604 R

FOREIGN PATENT DOCUMENTS 2547536 4/1976 Fed. Rep. of Germany ...... 562/535
49-92006 9/1974 Japan ................... 260/604 R
50-37719 4/1975 Japan ................... 562/534
50-12410 5/1975 Japan ................... 562/534

Primary Examiner—Werren B. Lone
Attorney, Agent, or Firm—Wenderoth, Lind & Ponack

[57]  ABSTRACT

In a process for preparing methacrylic acid by the vapor-phase catalytic oxidation of methacrolein or a methacrolein-containing mixture with molecular oxygen in the presence of an oxidation catalyst; the improvement wherein said process comprises a first-stage oxidation step of oxidizing methacrolein or a methacrolein-containing mixture as a starting material, a first-stage separating step of separating the resulting methacrylic acid from the reaction product obtained in the first-stage oxidation step, a second-stage oxidation step of oxidizing the mixture containing the unreacted methacrolein and obtained in the first-stage separating step, and a second-stage separating step of separating the resulting methacrylic acid from the reaction product obtained in the second-stage oxidation step, and with or without at least one additional oxidation step and separating step subsequent to the second-stage separating step, and wherein the conversion of methacrolein in the first-stage oxidation step is adjusted to 30–85 mole % and the final conversion of methacrolein is adjusted to at least 90 mole %.

6 Claims, 3 Drawing Figures

PROCESS FOR PREPARING METHACRYLIC ACID

This application is a continuation-in-part application of application Ser. No. 843,691 filed Oct. 19, 1977 now abandoned.

This invention relates to a process for preparing methacrylic acid. More specifically, it relates to a process for preparing methacrylic acid by the vapor phase catalytic oxidation of methacrolein or a methacrolein-containing mixture in the presence of a catalyst.

Some terms used in the present specification are defined as follows:

Anterior-stage oxidation step

A step in which a $C_4$ compound such as isobutylene or tertiary butanol is catalytically oxidized in the vapor phase to produce methacrolein.

Posterior-stage oxidation step

A step in which methacrolein or a methacrolein-containing mixture is catalytically oxidized in the vapor phase to produce methacrylic acid.

First-stage oxidation step

A step of performing the vapor-phase catalytic oxidation for the first time in the posterior-stage oxidation step.

First-stage separating step

A step in which methacrylic acid is separated from the reaction product of the first-stage oxidation step.

Second-stage oxidation step

A step in which the reaction mixture containing the unreacted methacrolein and obtained by the first-stage separating step is catalytically oxidized in the vapor phase.

Second-stage separating step

A step in which methacrylic acid is separated from the reaction product of the second-stage oxidation step.

Direct anterior/posterior stage method

A method for producing methacrylic acid which comprises introducing the methacrolein-containing mixture obtained in the anterior-stage oxidation step into the posterior-stage oxidation step without treating it for separation and purification.

Independent posterior-stage oxidation method

A method for producing methacrylic acid which comprises introducing methacrolein produced in advance into the posterior-stage oxidation step together with molecular oxygen.

Investigation concerning the production of methacrylic acid by vapor-phase catalytic oxidation have been extensively carried out in recent years, and an independent posterior-stage oxidation method using methacrolein as a raw material and a direct anterior/posterior stage method using isobutylene or tertiary butanol as a raw material have been suggested. The latter is considered basically advantageous over the former for the commercial production of methacrylic acid. However, if this method is performed using known posterior-stage oxidation catalysts, the yield of methacrylic acid is reduced by the unreacted materials such as isobutylene or tarry by-products contained in the reaction mixture of the anterior-stage oxidation step (see Japanese Laid-Open Patent Publication No. 111017/75). For this reason, the former has gained general acceptance.

It is known that the conventional posterior-stage oxidation catalysts give methacrylic acid in superior yields with superior selectivities when the conversion of methacrolein is 40 to 90%. In order to produce methacrylic acid with good efficiency, it is necessary to return the unreacted methacrolein to the reaction zone. This necessitates a step of separating methacrolein from the reaction mixture containing unreacted methacrolein and purifying it. This step is performed by separating and recovering methacrolein by such means as absorption with a solvent, or low-temperature processing, and purifying it by distillation, stripping, etc. However, the methacrolein contained in the reaction mixture is difficult to recover with good efficiency because it is generally in a low concentration. Moreover, a great amount of energy is consumed by heating or concentration in the separating and purifying procedures. In addition, since methacrolein having high polymerizability and an extremely acrid odor is separated by this step, special measures for the prevention of its polymerization and careful handling of the reaction mixture for preventing accidents are required.

It is an object of this invention to provide a process for preparing methacrylic acid by oxidizing methacrolein with good efficiency.

Another object of this invention is to produce methacrylic acid by a simplified process with reduced operational troubles and reduced energy losses.

Still another object of this invention is to provide a process for preparing methacrylic acid, which is suitable for the direct anterior/posterior stage oxidation heretofore considered to be difficult.

The present inventors have found the following facts as a result of investigations made in order to achieve these objects.

(1) The yield of methacrylic acid is reduced when the unreacted materials such as isobutylene or tarry by-products, which are contained in the reaction mixture of the anterior-stage oxidation, are introduced into the posterior-stage oxidation step. This is due mainly to the reduced conversion of methacrolein. The decrease of the selectivity of methacrylic acid is relatively small.

(2) When the conversion of methacrolein is elevated by the choice of the reaction conditions (for example, by decreasing the space velocity (SV) or elevating the reaction temperature) in an attempt to omit the step of separating and purifying the unreacted methacrolein in the second-stage oxidation, a part of methacrylic acid formed in the catalyst zone is converted to acetic acid, carbon monoxide, carbon dioxide and tarry substances by consecutive decomposition reactions or oxidation reaction, etc. Consequently, the selectivity of methacrylic acid is reduced, and a higher yield of methacrylic acid cannot be achieved. Moreover, this quickens the deterioration of the second-stage oxidation catalyst.

The present inventors hit upon an idea of dividing the second-stage oxidation by which methacrolein or a methacrolein-containing mixture is catalytically oxidized with molecular oxygen in the vapor phase to produce methacrylic acid. Thus, the present invention provides a process for preparing methacrylic acid, which comprises a first-stage oxidation step of oxidizing methacrolein or a methacrolein-containing mixture as a starting material, a first-stage separating step of separating the resulting methacrylic acid from the reaction product obtained in the first-stage oxidation step, a second-stage oxidation step of oxidizing the mixture containing the unreacted methacrolein and obtained in the first-stage separating step, and a second-stage separating step of separating the resulting methacrylic acid from the reaction product obtained in the second-stage oxidation step, with or without at least one additional oxidation step and separating step subsequent to the second-stage separating step.

The raw material for methacrylic acid used in this invention is methacrolein or a methacrolein-containing mixture. The methacrolein-containing mixture contains methacrolein obtained by the vapor-phase catalytic oxidation (the anterior-stage oxidation step) of a $C_4$ compound such as isobutylene or tertiary butanol, the unreacted material, inert gases, by-products, etc. This mixture is fed in the gaseous state into the posterior-stage oxidation step without separating methacrolein. Various methods have been developed in the past to produce the methacrolein-containing mixture in the anterior-stage oxidation step. In the present invention, any such mixtures obtained by the known methods can be used. For example, suitable used in the present invention are methacrolein-containing mixtures which are obtained by catalytically oxidizing $C_4$ compounds in the vapor phase at a reaction temperature of 250° to 700° C. and a pressure ranging from atmospheric pressure to 10 atmospheres in the presence or absence of an inert gas such as steam, nitrogen or carbon dioxide while maintaining the space velocity (SV) of the entire starting mixture fed at 200 to 10000 $hr^{-1}$. When isobutylene, tertiary butanol or a mixture of these is used as the $C_4$ compound, and an $(Mo)_a(Bi)_b(Fe)_c(Co$ and/or $Ni)_d(Q)_e(R)_f(X)_g(O)_h$ type catalyst (wherein Q represents at least one element selected from P, As and B, R represents at least one element selected from alkali metals, alkaline earth metals and Tl, and X represents at least one element selected from Cr, V, Nb, Ta, W, Sb, Th, Ce, Ti, Te, Zn, Ge, Sn, Ga, La, In, Al, Cd, Pd, Mn, Pb, Ag, Zr, Cu, Nd, U, Si, Se, Hg, Au and Sm, and a, b, c, d, e, f, g and h represent the number respectively of Mo, Bi, Fe, Co and/or Ni, Q, R, X and O atoms and when $a=12$, $b=0.1-10$, $c=0.5-40$, $d=0.5-15$, $e=0-5$, $f=0.01-5$ and $g=0-12$, and h is the number of oxygen atoms which satisfies the atomic valences of the other elements) is used as a catalyst, if desired as supported on a carrier or diluted, the conversion of the $C_4$ compound can be increased, and the oxidation reaction in the posterior-stage oxidation step proceeds with better efficiency. The conversion of the $C_4$ compound can be enhanced and at the same time, the formation of by-product tarry substances can be extremely inhibited, if there is used the catalyst disclosed in U.S. Pat. No. 4,186,152 or German Patent Provisional Publication No. 2735414.9, that is, the catalyst having the composition $Mo_aBi_bFe_cCo_dNi_eQ_fR_gX_hZ_iO_j$ (wherein Q represents at least one element selected from Be, Nd, Ag and Au, R represents at least one element selected from K, Rb, Cs and Tl, X represents at least one element selected from P, As and B, Z represents at least one element selected from Ce, Ti, Te, Zn, Ge, Sn, Cr, Ga, La, In, Al, Cd, Pd, Mn, V, Pb, Nb, Zr, Cu and U, and a, b, c, d, e, f, g, h, i and j represent the number respectively of Mo, Bi, Fe, Co, Ni, Q, R, X, Z and O atoms, and when $a=12$, $b=0.1-10$, $c=0.5-40$, $d=0-12$, $e=0-12$, $d+e=0.5-15$, $f=0.1-35$, $g=0.01-5$, $h=0-5$ and $i=0-12$ and j is the number of oxygen atoms which satisfies the atomic valences of the other elements). This makes possible a very effective oxidation reaction in the posterior-stage oxidation step.

Methacrolein or a methacrolein-containing mixture is first fed into the first-stage oxidation step wherein a part of the methacrolein is catalytically oxidized in the vapor phase in a customary manner to form methacrylic acid. For example, methacrylic acid can be easily obtained by catalytically oxidizing methacrolein in the vapor phase with molecular oxygen or air in the presence of a known catalyst in the presence or absence of an inert gas such as steam, nitrogen or carbon dioxide gas, as in the case of the anterior-stage oxidation step. The preferred reaction conditions at this time are: the concentration of methacrolein, 0.001 to 25% by volume; the molar ratio of methacrolein to oxygen, 1:0.1–25, the reaction temperature, 250° to 500° C.; the space velocity (SV), 100–10000 $hr^{-1}$ (STP base); the reaction pressure, atmospheric pressure to 10 atmospheres. In this reaction, high conversions tend more to cause decomposition of methacrylic acid or the formation of tarry substances by enhanced consecutive reactions of methacrylic acid. Preferably, therefore, the conversion of methacrolein in the first-stage oxidation step should be adjusted to 30 to 85 mole%, preferably 40 to 80 mole%.

The catalyst used in the posterior-stage oxidation step may be any material which has the ability to catalyze the oxidation of methacrolein to methacrylic acid. Examples are the $P_aMo_bX_cY_dO_e$-type catalysts (wherein X represents at least one element selected from alkali metals, alkaline earth metals, Tl, As and Sb, Y represents at least one element selected from Si, Cr, Al, Ge, Ti, V, W, Bi, Nb, B, Ga, Pb, Sn, Co, Pd, Zr, Te, Fe, Ni, In, Cu, Ag, Mn, La, Nd, Ta, Sm, Hf, Re, Rh, Zn, Cd, S, Se, Ce, Th and U, and a, b, c, d and e represent the number of P, Mo, X, Y and O atoms respectively, and when $b=12$, $a=0.1-8$, $c=0-10$, $d=0-12$, and $c+d=0.01-12$, and e is the number of oxygen atoms which satisfies the atomic valences of the other elements) disclosed in U.S. Pat. Nos. 3,686,294, 3,795,703, 3,882,047, 3,976,688 and 4,075,244, and German Laid-Open Patent Applications Nos. P 2511076.3 and P 2547314.7; and the $P_aPd_bX_cO_d$-type catalysts (wherein X represents at least one element selected from Pb, Bi, Pb, Cr, Fe, Ni, Co, Mn, Sn, U and Ba, a, b, c and d respectively represent the number of P, Pd, X and O atoms, and when $b=1$, $a=1-42$ and $c=0-15$, and d is the number of oxygen atoms which satisfies the atomic valences of the other elements) disclosed in Japanese Patent Publications Nos. 33614/77, 431819/77, 38539/77, 39814/77, 3371/78, and 24050/78.

The reaction mixture formed in the first-stage oxidation step is then fed into the first-stage separating step where methacrylic acid is separated in a customary manner. Available separating methods are, for example, an extraction method, a low-temperature processing method, an absorption method, and an adsorption method. Of these, the absorption method using a solvent which readily absorbs methacrylic acid contained in the reaction mixture, for example, water, esters, ketones and organic acids, is preferred. When water is used as the absorption solvent, the oxidation reaction of methacrolein in the second-stage oxidation step proceeds effectively because water is easy to handle and permits the absorption of by-product tarry substances and acids other than methacrylic acid in the reaction mixture.

The mixture containing unreacted methacrolein which is left after the separation of methacrylic acid from the reaction mixture obtained in the first-stage oxidation step is fed usually in the gaseous state into the second-stage oxidation step. At this time, the reaction conditions can be adjusted by optionally feeding methacrolein, oxygen, steam and other inert substances. The reaction conditions in the second-stage oxidation step may be the same as or different from those in the first-stage oxidation step if methacrolein can be catalytically oxidized in the vapor phase to methacrylic acid under such conditions. Any conditions suitable for this step can be selected as desired.

A greater portion of the unreacted methacrolein is thus oxidized to methacrylic acid in the second-step oxidation step. If methacrolein is oxidized to a high conversion by conventional methods, large quantities of by-products such as acetic acid, carbon monoxide or tarry substances are formed by consecutive decomposition or oxidation of methacrylic acid formed in the reaction system. According to the process of this invention, the formation of such by-products can be greatly inhibited because methacrylic acid formed in the first-stage oxidation step is separated in the first-stage separating step. Furthermore, the process of this invention can prevent the deterioration of the oxidation catalyst. At this stage, the reaction can be usually performed until the conversion of methacrolein reaches approximately 100%. However, when the conversion of methacrolein in the first-stage oxidation step is low or methacrylic acid is selectively separated in the first-stage separating step, a large amount of the unreacted methacrolein or impurities such as tarry substances remain in the mixture. Hence, it is sometimes disadvantageous or difficult to increase the conversion of methacrolein to a large extent in the second-stage oxidation step. In such a case, the mixture containing unreacted methacrolein which has been subjected to the second-stage separating step is fed into a third-stage oxidation step.

Thus, according to this invention, the conversion of methacrolein can be increased to at least 90 mole%, preferably at least 95 mole%, while preventing the decomposition of the resulting methacrylic acid.

The reaction mixture obtained in the second-stage oxidation step is sent to the second-stage separating step where methacrylic acid is separated. The second-stage separating step may be the same as or different from the first-stage separating step if it can permit the separation of methacrylic acid. However, when the separation of methacrylic acid is performed by using an absorption solvent, it is preferred to use the same absorbing solvent, especially water. The methacrylic acid-containing solution withdrawn from the second-stage separating step can also be used as the absorbing solvent in the first-stage separating step.

On example of the process of this invention is specifically illustrated by FIG. 1 of the accompanying drawings which is a diagram for illustrating the process for methacrylic acid production in accordance with this invention.

A raw material for the production of methacrolein is fed into a reaction tower 2 (anterior-stage oxidation step) from a line 1. The material is catalytically oxidized in the vapor phase in the reaction tower 2, and the resulting methacrolein-containing mixture is introduced into a reaction tower 4 (first-stage oxidation step) of a posterior-stage oxidation step through a line 3. A part of the methacrolein is oxidized to methacrylic acid in the reaction tower 4. The reaction mixture is sent to a separating tower 6 (first-stage separating step) through a line 5. Methacrylic acid is absorbed by a solvent fed from a line 14, and recovered through a line 16. The mixture containing unreacted methacrolein is introduced through a line 7 into a reaction tower 8 (second-stage oxidation step) where the unreacted methacrolein is almost entirely oxidized. The reaction mixture is sent through a line 9 to a separating tower 10 (second-stage separating step) where methacrylic acid is absorbed by a solvent fed from a line 12. The solvent is then sent to the separation tower 6 through the line 14. If the unreacted methacrolein is not sufficiently oxidized in the second-stage oxidation step and remains in a more than negligible amount, the methacrolein-containing mixture which has left a separating tower 10 through a line 11 is introduced into a third-stage oxidation step (not shown) and then into a third-stage separating step (not shown). If desired, methacrolein, air, oxygen, steam and other inert substances may be introduced into the reaction towers 4 and 8 through lines 17 and 18. Lines 13 and 15 are for recycling of the solvent.

The present invention can afford methacrylic acid in a high yield with a high conversion of methacrolein by a simplified process which does not require steps of separating and purifying methacrolein that is difficult to handle. When methacrylic acid is produced by the direct anterior/posterior stage method, a small amount of by-product methacrylic acid in the anterior-stage oxidation step can be effectively recovered. Particularly, when methacrylic acid is separated by an absorbing solvent, steam already introduced can be effectively utilized without condensation by controlling the temperature of the top of the separating tower. Since the posterior-stage oxidation step is divided into multiple steps, the formation of by-products can be inhibited, and the activity of the catalyst can be fully exhibited, by properly selecting the reaction conditions in the individual steps.

Figure 1:
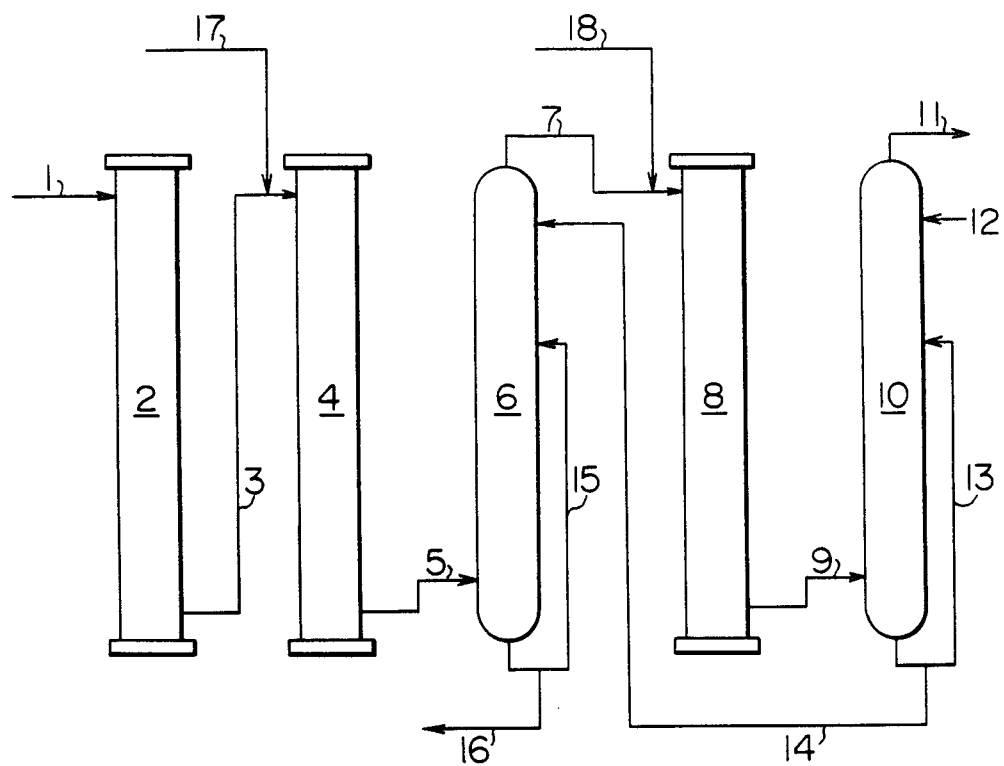

The following Examples more specifically illustrate the present invention.

EXAMPLE 1

Methacrylic acid was produced from isobutylane as a raw material by the direct anterior/posterior stage method under the reaction conditions set forth below.

(1) Anterior-stage oxidation step:

100 ml of an Mo-Bi-Fe-Co-Ni-Be-P-K type catalyst [Mo:Bi:Fe:Co:Ni:Be:P:K = 12:1:12:4:1:3:0.5:1 (atomic ratio), calcined at 600° C., catalyst particle diameter 4–8 mesh] was packed into a stainless steel reaction tube with an inside diameter of 2.5 cm and a length of 60 cm. The reaction tube was heated to 340° C. in a metal bath, and a starting gaseous mixture of isobutylene, air and steam in a molar ratio of 4:55:41 was passed through the reaction tube at a space velocity of 2000 $hr^{-1}$.

(2) Posterior-stage oxidation step (first-stage oxidation):

100 ml of an Mo-P-Cs-Cr type catalyst [Mo:P:Cs:Cr = 1:0.16:0.16:0.16 (atomic ratio), calcined at 450° C., catalyst particle diameter 4–8 mesh] was packed into a stainless steel reaction tube with an inside diameter of 2.5 cm and a length of 60 cm. The reaction tube was heated to 335° C. in a metal bath, and the reaction mixture containing methacrolein which had been obtained in the anterior-stage oxidation step was passed through the reaction tube.

(3) First-stage separating step:

The reaction mixture containing unreacted methacrolein which had left the first-stage oxidation step was fed into a separating tower, and contacted countercurrent with water heated at about 83° C. and fed from the top of the tower. Methacrylic acid, acetic and other by-product acids were separated from the bottom of the tower by absorption.

(4) Posterior-stage oxidation (second-stage oxidation) step:

The mixture containing unreacted methacrolein which had left the first-stage separating step was passed through the same reactor as used in the first-stage oxidation step which had been packed with 100 ml of the same catalyst and heated to 320° C. in a metal bath.

(5) Second-stage separating step:

The reaction mixture which had left the second-stage oxidation step was sent to a separating step, and contacted concurrently with water at room temperature which was fed from the top of the tower.

As a result of performing the process of this invention by steps (1) to (5), the following results were obtained.
Conversion of methacrolein: 98.0 mole%
Yield of methacrylic acid based on methacrolein: 74.6 mole%
Selectivity of methacrylic acid: 76.1%
Conversion of isobutylene 100 mole%
Yield of methacrylic acid based on isobutylene: 58.2 mole%

EXAMPLE 2

The procedure of Example 1 was repeated except that in the anterior-stage oxidation step, an Mo-Bi-Fe-Co-Ni-Ag-P-K type catalyst [Mo:Bi:Fe:Co:Ni:Ag:P:K:=12:1:12:4:1:1:0.5:1 (atomic ratio), calcined at 600° C., catalyst particle size diameter 4–8 mesh] was used.

The results were as follows:
Conversion of methacrolein: 97.5 mole%
Yield of methacrylic acid based on methacrolein: 73.4 mole%
Selectivity of methacrylic acid 75.3%
Conversion of isobutylene: 100 mole%
Yield of methacrylic acid based on isobutylene: 57.0 mole%

Comparative Example 1

The procedure of Example 1 was repeated except that the second-stage oxidation step was omitted (that is, in accordance with the conventional method).

The results were as follows:
Conversion of methacrolein: 80.8 mole%
Yield of methacrylic acid based on methacrolein: 60.5 mole%
Selectivity of methacrylic acid: 74.9%
Conversion of isobutylene: 100 mole%
Yield of methacrylic acid based on isobutylene: 47.2 mole%

It is clear from these data that the steps of separating and purifying unreacted methacrolein are required in order to utilize methacrolein effectively in the conventional method.

Comparative Example 2

The procedure of Example 1 was repeated except that the first-stage separating step was omitted and the reaction mixture from the first-stage oxidation step was immediately introduced into the second-stage oxidation step without treatment.

As a result, the conversion of methacrolein was 91.2 mole%, but the amounts of acetic acid, carbon monoxide and tarry substances formed as by-products were large. The yield of methacrylic acid based on methacrolein decreased to 59.6 mole%, and the selectivity of methacrylic acid decreased to 65.3%. The conversion of isobutylene was 100 mole%, and the yield of methacrylic acid based on isobutylene was 46.5 mole%.

EXAMPLE 3

Figure 2:
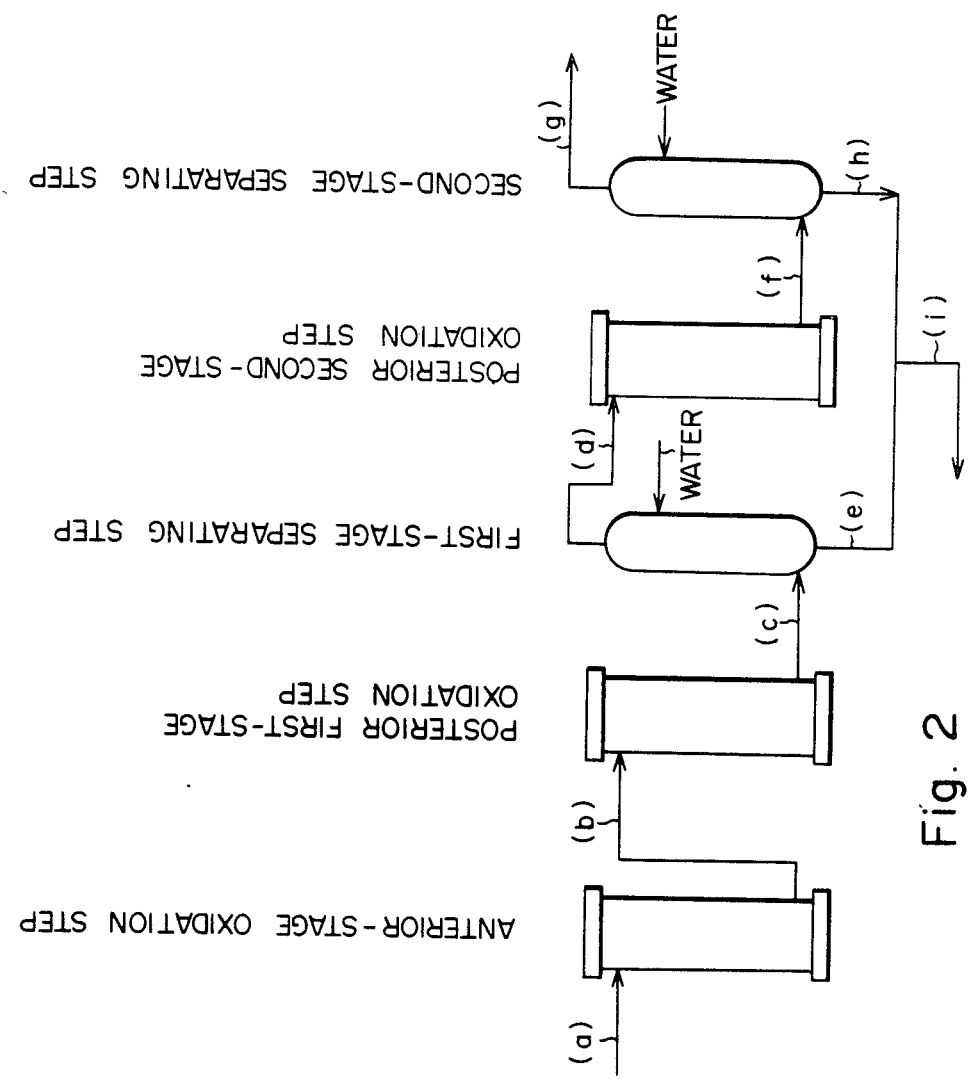
FIG. 2 is a diagram for illustrating the process for methacrylic acid production in accordance with Examples 3 to 7.

Example 1 was repeated except that the catalyst used in the posterior-stage oxidation step was changed to the Mo-P-V-Cs type catalyst (atomic ratio of Mo:P:V:Cs=12:2:1:2; fired at 450° C.; particle diameter 4–8 mesh) disclosed in U.S. Pat. No. 4,075,244, and the temperature of the metal bath in the reactor was changed to 318° C. in the first stage and to 294° C. in the second stage. This process is shown in FIG. 2 of the accompanying drawings.

The amounts of isobutylene, methacrolein and methacrylic acid withdrawn from the individual steps, per mole of the starting isobutylene introduced into the anterior-stage oxidation step [i.e., the amounts of these in lines (a) to (i)] were as shown in Table 1 below.

TABLE 1

| Line | Amount (moles) | | |
|---|---|---|---|
| | Isobutylene | Methacrolein | Methacrylic acid |
| (a) | 1 | 0 | 0 |
| (b) | 0.022 | 0.781 | 0.016 |
| (c) | 0 | 0.156 | 0.514 |
| (d) | 0 | 0.155 | 0 |
| (e) | 0 | 0.001 | 0.514 |
| (f) | 0 | 0.025 | 0.102 |
| (g) | 0 | 0.024 | 0 |
| (h) | 0 | 0.001 | 0.102 |
| (i) | 0 | 0.002 | 0.616 |

It is seen from the data given in Table 1 that the conversion of methacrolein $$\left( \frac{(b)_{MAL} - (g)_{MAL} - (i)_{MAL}}{(b)_{MAL}} \times 100 \right)$$

in the posterior-stage oxidation step was 96.7%, the yield of methacrylic acid based on methacrolein $$\left( \frac{(i)_{MAA}}{(b)_{MAL}} \times 100 \right)$$

was 78.9%, and the selectivity of methacrylic acid was 81.6%, and that based on the starting isobutylene, the conversion of isobutylene was 100%, and the yield of methacrylic acid $$\left( \frac{(i)_{MAA}}{(a)_{C4}} \right)$$

was 61.6%. In the above formulae, $^{(b)}$MAL means the amount of methacrolein at the line (b), and the other symbols should be understood similarly [for example, (i)$_{MAA}$ means the amount of methacrylic acid in line (i)].

EXAMPLES 4 TO 7

Example 3 was repeated except that the catalyst and the reaction temperature (the temperature of the metal bath) used in the posterior-stage oxidation step were varied as shown in Table 2. The results are also shown in Table 2.

TABLE 2

| Example | Catalyst | Temperature of the metal bath (°C.) 1st stage | Temperature of the metal bath (°C.) 2nd stage | Conversion of isobutylene (%) | Reaction results in the posterior-stage oxidation step Conversion of methacrolein (%) | Yield of methacrylic acid (%) | Selectivity of methacrylic acid (%) |
|---|---|---|---|---|---|---|---|
| 4 | Mo$_{12}$P$_2$V$_1$Rb$_2$Sr$_{0.5}$ (U.S. Pat. No. 4,075,244) | 334 | 318 | 100 | 96.4 | 75.4 | 78.2 |
| 5 | Mo$_{12}$P$_1$As$_1$ (U.S. Pat. No. 3,686,294) | 329 | 320 | 100 | 97.2 | 67.1 | 69.0 |
| 6 | Mo$_{12}$Pd$_1$Sb$_{14}$ (U.S. Pat. No. 3,646,127) | 337 | 335 | 100 | 94.9 | 57.2 | 60.3 |
| 7 | Mo$_{12}$P$_1$Zr$_1$Cs$_{0.2}$ (Japanese Laid-Open Publication No. 70318/75) | 350 | 343 | 100 | 96.7 | 64.7 | 66.9 |

EXAMPLE 8

Figure 3:
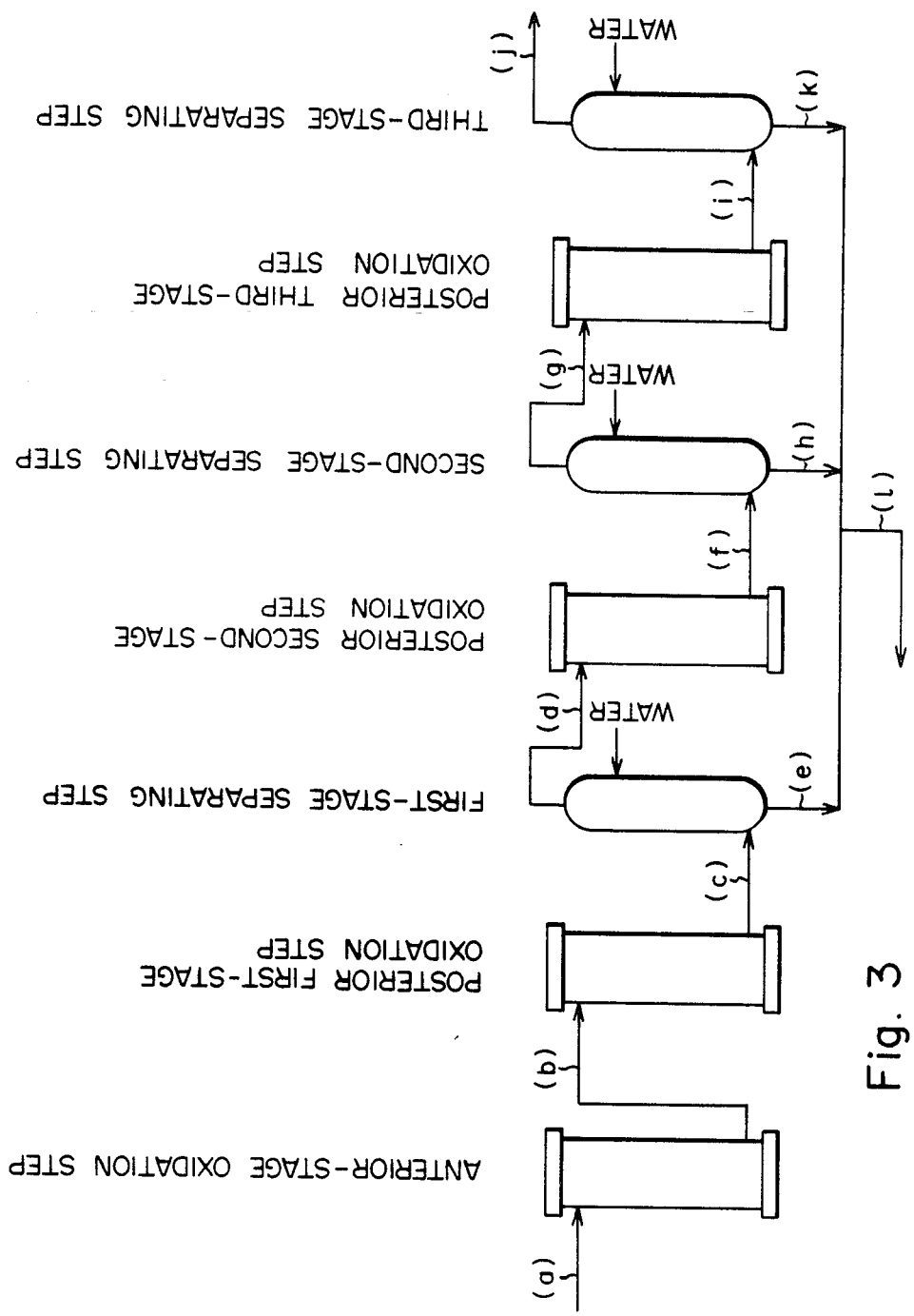
FIG. 3 is a diagram for illustrating the process for methacrylic acid production in accordance with Example 8.

Example 1 was repeated except that as shown in FIG. 3, a posterior third-stage oxidation step and a third-stage separating step were attached to the process shown in FIG. 2. In this process, the temperature of the metal bath was set at 280° C. in the first-stage oxidation step, at 305° C. in the second-stage oxidation step, and at 315° C. in the third-stage oxidation step.

The amounts of isobutylene, methacrolein and methacrylic acid withdrawn per mole of the starting isobutylene in the individual steps were as shown in Table 3.

TABLE 3

| Line | Amount (moles) Isobutylene | Methacrolein | Methacrylic acid |
|---|---|---|---|
| (a) | 1 | 0 | 0 |
| (b) | 0.022 | 0.781 | 0.016 |
| (c) | 0 | 0.524 | 0.226 |
| (d) | 0 | 0.523 | 0 |
| (e) | 0 | 0.001 | 0.226 |
| (f) | 0 | 0.197 | 0.255 |
| (g) | 0 | 0.196 | 0 |
| (h) | 0 | 0.001 | 0.255 |
| (i) | 0 | 0.026 | 0.122 |
| (j) | 0 | 0.004 | 0 |
| (k) | 0 | 0.022 | 0.122 |
| (l) | 0 | 0.024 | 0.603 |

It is seen from the data given in Table 3 that the conversion of methacrolein $$\left( \frac{^{(b)}MAL - ^{(j)}MAL - ^{(l)}MAL}{^{(b)}MAL} \times 100 \right)$$

in the posterior-stage oxidation step was 96.4%, the yield of methacrylic acid based on methacrolein $$\left( \frac{^{(l)}MAA}{^{(b)}MAL} \times 100 \right)$$

was 77.2%, and the selectivity of methacrylic acid was 80.0%. Based on the starting isobutylene, the conversion of isobutylene was 100%, and the yield of methacrylic acid was 60.3%.

From the data shown in Table 3, the results of the reactions in the individual oxidation steps in the posterior-stage oxidation step were calculated. The results are shown in Table 4.

TABLE 4

| | Conversion of methacrolein (%) | Yield of methacrylic acid (%) | Selectivity of methacrylic acid (%) |
|---|---|---|---|
| Posterior first-stage oxidation step | 32.9 | 26.9* | 81.8 |
| Posterior second-stage oxidation step | 62.3 | 48.8 | 78.3 |
| Posterior third-stage oxidation step | 86.7 | 62.2 | 71.7 |

*Calculated in accordance with
$\frac{^{(c)}MAA - ^{(b)}MAA}{^{(b)}MAL} \times 100$

What we claim is:

1. In a process for preparing methacrylic acid by the vapor-phase catalytic oxidation of methacrolein or a methacrolein-containing mixture with molecular oxygen in the presence of an oxidation catalyst; the improvement wherein said process comprises a first-stage oxidation step of oxidizing methacrolein or a methacrolein-containing mixture as a starting material, a first-stage separating step of separating the resulting methacrylic acid from the reaction product obtained in the first-stage oxidation step, to form a mixture containing unreacted methacrolein, a second-stage oxidation step of oxidizing said mixture containing the unreacted methacrolein, and a second-stage separating step of separating the resulting methacrylic acid from the reaction product obtained in the second-stage oxidation step, and with or without at least one additional oxidation step and separating step subsequent to the second-stage separating step, and wherein the conversion of methacrolein in the first-stage oxidation step is adjusted to 30–85 mole% and the final conversion of methacrolein is adjusted to at least 90 mole%.

2. The process of claim 1 wherein the starting methacrolein-containing mixture is the reaction product obtained by the vapor-phase catalytic oxidation of isobutylene, tertiary butanol or a mixture of these.

3. The process of claim 1 wherein the conversion of methacrolein in the first-stage oxidation step is 40–80 mole%.

4. The process of claim 1 wherein the methacrylic acid is separated in each separating step by using an absorbing solvent.

5. The process of claim 1 wherein the catalyst contains (a) P and Mo or (b) P and Pd as essential ingredients.

6. The process of claim 1 wherein the starting methacrolein-containing mixture is the reaction product obtained by catalytically oxidizing isobutylene, tertiary butanol or a mixture of these in the vapor phase in the presence of a catalyst containing as essential ingredients (a) Mo, (b) Bi, (c) Fe, (d) Co and/or Ni and (e) at least one of alkali metals, alkaline earth metals or Tl.

* * * * *